US011317609B2

(12) United States Patent
Menkes et al.

(10) Patent No.: US 11,317,609 B2
(45) Date of Patent: *May 3, 2022

(54) ACOUSTICALLY ENHANCED PET ANIMAL COLLAR FOR HEALTH AND VITAL SIGNS MONITORING, ALERT AND DIAGNOSIS (71) Applicant: PetPace Ltd., Ramat Hasharon (IL)

(72) Inventors: Avi Menkes, Ramat Hasharon (IL); Michael Bukchin, Haifa (IL)

(73) Assignee: PETPACE LTD., Ramat Hasharon (IL)

( * ) Notice: Subject to any disclaimer, the term of this patent is extended or adjusted under 35 U.S.C. 154(b) by 429 days.

This patent is subject to a terminal disclaimer.

(21) Appl. No.: 16/438,468

(22) Filed: Jun. 12, 2019

(65) Prior Publication Data
US 2019/0289827 A1 Sep. 26, 2019

Related U.S. Application Data (63) Continuation of application No. 13/743,383, filed on Jan. 17, 2013, now Pat. No. 10,440,938.

(51) Int. Cl.
*A01K 29/00* (2006.01)
*A01K 27/00* (2006.01)
*A61B 5/00* (2006.01)
*A61B 5/0205* (2006.01)
*A61B 5/01* (2006.01)
(Continued)

(52) U.S. Cl.
CPC .......... *A01K 29/005* (2013.01); *A01K 27/009* (2013.01); *A61B 5/0002* (2013.01); *A61B 5/0205* (2013.01); *A61B 5/01* (2013.01); *A61B 5/024* (2013.01); *A61B 5/0816* (2013.01); *A61B 5/11* (2013.01); *A61B 2503/40* (2013.01)

(58) Field of Classification Search
CPC .. A01K 15/021; A01K 15/022; A01K 15/023; A01K 15/029; A01K 15/04; A01K 27/00; A01K 27/001; A01K 27/009; A01K 29/00; A01K 29/005
See application file for complete search history.

(56) References Cited

U.S. PATENT DOCUMENTS

5,002,060 A * 3/1991 Nedivi ................. A61B 5/0205
310/329
5,559,498 A * 9/1996 Westrick ............... A01K 15/023
340/573.3
(Continued)

*Primary Examiner* — Thanh Pham
(74) *Attorney, Agent, or Firm* — Mark M. Friedman (57) ABSTRACT An acoustically enhanced collar for monitoring vital signs of a pet animal, may comprise an elastic band having a working surface configured to wrap around a neck of a pet animal and an oppositely faced rear surface, at least one sensor element situated along a circumference of the band and configured to measure at least one bioparameter from the following bioparameters: temperature, heart rate, respiration rate, movement; at least one acoustic concentrator projecting as a bump toward the neck from the working surface on a first side of the at least one sensor element; at least one acoustic concentrator projecting as a bump toward the portion from the working surface on a second side of the at least one sensor element and acoustic balancers projecting from the rear surface at least partly behind the acoustic concentrators. Preferably, the acoustic concentrators and balancers have a base end having an "X" shape.

20 Claims, 5 Drawing Sheets

(51) Int. Cl.
  *A61B 5/024* (2006.01)
  *A61B 5/08* (2006.01)
  *A61B 5/11* (2006.01)

(56) References Cited

U.S. PATENT DOCUMENTS

| | | | | |
|---|---|---|---|---|
| 6,113,539 A | * | 9/2000 | Ridenour | A61B 5/0002 |
| | | | | 128/903 |
| 6,830,014 B1 | * | 12/2004 | Lalor | A01K 27/009 |
| | | | | 119/720 |
| 2008/0076994 A1 | * | 3/2008 | Hoarau | A61B 5/6826 |
| | | | | 600/344 |

* cited by examiner

```
┌─────────────────────────────────────────┐
│            METHOD - 100                 │
└─────────────────────────────────────────┘
```

PROVIDING AN ELASTIC BAND CONFIGURED TO WRAP AROUND A PORTION OF THE PET ANIMAL AND HAVING A WORKING SURFACE AND A REAR SURFACE, AT LEAST ONE SENSOR ELEMENT SITUATED AT ONE OR MORE REGIONS ALONG A CIRCUMFERENCE OF THE BAND AND CONFIGURED TO MEASURE AT LEAST ONE BIOPARAMETER FROM THE FOLLOWING BIOPARAMETERS: TEMPERATURE, HEART RATE, RESPIRATION RATE, MOVEMENT

↓ 110

CONFIGURING THE ELASTIC BAND WITH AT LEAST ONE ACOUSTIC CONCENTRATOR PROJECTING FROM THE WORKING SURFACE TOWARD THE PORTION OF THE PET ANIMAL, THE AT LEAST ONE ACOUSTIC CONCENTRATOR SITUATED AT THE ONE OR MORE REGIONS ALONG THE CIRCUMFERENCE AND ON A FIRST SIDE OF THE AT LEAST ONE SENSOR

↓ 120

CONFIGURING THE ELASTIC BAND WITH AT LEAST ONE ACOUSTIC BALANCER PROJECTING FROM THE REAR SURFACE AND SITUATED AT THE ONE OR MORE REGIONS ALONG THE CIRCUMFERENCE AND ON A SECOND SIDE OF THE AT LEAST ONE SENSOR ELEMENT, THE AT LEAST ONE LEFT ACOUSTIC BALANCER LOCATED IN A POSITION ALONG THE CIRCUMFERENCE AT LEAST PARTLY BEHIND THE AT LEAST ONE ACOUSTIC CONCENTRATOR

↓ 130

TRANSMITTING ELECTRONIC SIGNALS FROM THE SENSOR ELEMENTS TO A PROCESSOR, THE SIGNALS REFLECTING VITAL SIGN MEASUREMENTS OF THE PET ANIMAL

ACOUSTICALLY ENHANCED PET ANIMAL COLLAR FOR HEALTH AND VITAL SIGNS MONITORING, ALERT AND DIAGNOSIS

FIELD AND BACKGROUND OF THE INVENTION

The present invention relates to apparatuses and methods for monitoring vital signs and health of animals, and, more particularly for monitoring the health and vital signs of pet animals, such as dogs and cats, and doing so using a specially designed collar.

When animals, including pets such as dogs and cats, are sick they tend by nature to withdraw and hide since they feel defenseless. This behavior makes treatment of the animal significantly more difficult. With regard to pet animals, such as dogs and cats, it is known for veterinarians to check the vital signs of a sick dog or a sick cat. However, this tends to occur long after the animal has contracted the medical problem either because the dog or cat was hiding and/or because it takes time to reach the veterinarian. Early detection is often not achieved yet is very important in order to achieve less suffering of the pet and less likelihood of acute disease, which can develop if detection occurs late. Regarding ear infections in a dog, for example, according to Veterinary Pet Insurance (VPI), this is the most common medical condition affecting dogs in 2010 and "identifying changes or redness early will help dogs and cats avoid more irritating, painful and expensive ear infections. The longer a problem is allowed to persist, the more difficult it is to treat.".

Moreover, stray dogs and cats, as well as dogs and cats whose owners are not constantly with them as a practical matter, and dogs and cats whose owners are on vacation, are more vulnerable to contracting an illness, exhibiting hiding behavior patterns and decreasing the chances of timely medical intervention.

In addition, monitoring the health of captive animals, for example animals in zoos, is an arduous and expensive task. Although Applicant has filed a patent application for a pet collar that is adjustable, there is a compelling need using a non-invasive apparatus to capture the different sounds such as pulse, respiration, panting, vomiting and more made by a pet animal or other captive animals. The sounds tend to be very low frequency signals signals. If one were to utilize a very sensitive sensor on the pet's neck to capture these signals/vibrations, one would have to make the collar very tight around the neck, which is not practical with regard to the animal's behavior and comfort.

There is a compelling need to have an apparatus and method that will provide early detection and diagnosis of pet animals such as dogs and cats, and to do so accurately and efficiently without interfering with the comfort and behavior of the animal.

SUMMARY OF THE PRESENT INVENTION

One aspect of the present invention is an acoustically enhanced collar for monitoring vital signs of a pet animal, comprising an annular band comprising a layer of an elastic material, the band having a working surface configured to wrap around a portion of a pet animal and a rear surface facing an opposite direction to the working surface; at least one sensor element situated at one or more regions along a circumference of the band and configured to measure at least one bioparameter from the following bioparameters: temperature, heart rate, respiration rate, movement; at least two acoustic concentrators projecting toward a body portion of the pet animal from the working surface at the one or more regions along the circumference; at least two acoustic balancers projecting from the rear surface at the one or more regions along the circumference, the at least two acoustic balancers situated at a region along the circumference at least partly behind the at least two acoustic concentrators, each of the at least two acoustic concentrators wider at a concentrator base end adjacent the working surface than at a concentrator top end, each of the at least two acoustic balancers wider at a balancer base end adjacent the rear surface than at a balancer top end.

A further aspect of the present invention is a method of monitoring vital signs of a pet animal, the method comprising providing an elastic band configured to wrap around a portion of the pet animal and having a working surface and a rear surface, at least one sensor element situated at one or more regions along a circumference of the band and configured to measure at least one bioparameter from the following bioparameters: temperature, heart rate, respiration rate, movement; configuring the elastic band with at least one acoustic concentrator projecting from the working surface toward the portion of the pet animal, the at least one acoustic concentrator situated at the one or more regions along the circumference and on a first side of the at least one sensor; configuring the elastic band with at least one acoustic balancer projecting from the rear surface and situated at the one or more regions along the circumference and on a second side of the at least one sensor element, the at least one left acoustic balancer located in a position along the circumference at least partly behind the at least one acoustic concentrator; and transmitting electronic signals from the sensor elements to a processor, the signals reflecting vital sign measurements of the pet animal.

A still further aspect of the present invention is an acoustically enhanced collar for monitoring vital signs of a pet animal, comprising a band comprising a layer of an elastic material, the band having a working surface configured to wrap around a portion of a pet animal and an oppositely faced rear surface; at least one sensor element situated at one or more regions along a circumference of the band and configured to measure at least one bioparameter from the following bioparameters: temperature, heart rate, respiration rate, movement; at least one acoustic concentrator projecting as a bump toward the portion of the working surface, the at least one acoustic concentrator situated at the one or more regions along the circumference and on on a first side of the at least one sensor element; and at least one acoustic balancer projecting as a bump from the rear surface and situated at the one or more regions along the circumference and on a second side of the at least one sensor element.

These and other features, aspects and advantages of the present invention will become better understood with reference to the following drawings, descriptions and claims.

BRIEF DESCRIPTION OF THE DRAWINGS

Various embodiments are herein described, by way of example only, with reference to the accompanying drawings, wherein.

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention, since the scope of the invention is best defined by the appended claims.

The present invention generally provides a collar for pet animals such as dogs and cats. The collar mat include an annular band comprising a layer of an elastic material, the band having a working surface configured to wrap around a neck or other portion of a pet animal and a rear surface facing an opposite direction to the working surface. The collar may also have at least one sensor element situated at one or more regions along a circumference of the band and configured to measure at least one bioparameter from the following bioparameters: temperature, heart rate, respiration rate, movement. At least one acoustic concentrator, in the form of a bump, may project toward the neck or other body portion of the pet animal from the working surface at the one or more regions along the circumference. In addition, at least one acoustic balancer may projecting from the rear surface at the one or more regions along the circumference. The at least one acoustic balancer may be situated at a region along the circumference at least partly behind and preferably directly behind the at least one acoustic concentrators. Each of the acoustic concentrators may be wider at a concentrator base end adjacent the working surface than at a concentrator top end and likewise each of the acoustic balancers may be wider at a balancer base end adjacent the rear surface than at a balancer top end. Preferably, the acoustic concentrators and preferably also the balancers have an X-shaped cross-section.

The collar may have sensor elements that can be activated remotely to check vital signs of the animal (such as respiration, pulse, temperature and movement) and a processor that can interpret the results of multiple vital sign readings. The collar may also have a two way communication device attached or integrated thereto that can alert the pet owner, a veterinarian or the authorities, when appropriate, that a pet animal is suffering from a particular condition or is exhibiting suspicious behavior or movements. This way, a veterinarian can remotely take a particular vital sign measurement when alerted of the data by signalling the processor to actuate a particular sensor element. The sensor elements that may be embedded in the band of the collar may gather data that can be processed on the collar itself or transmitted to a remote terminal, which can be a home computer, a handheld device, or a main server computer. In order to dramatically improve the system gain, sensitivity and signal to noise ratio (SNR), an elastic layer may absorb noise from friction due to movement of the animal's head.

In contrast to prior art pet animal collars, which do not measure vital signs, the pet collar of the present invention may measure vital signs of the pet animal. For example, it may measure, heart rate, respiration rate, blood pressure, temperature, movement, etc. In further contrast to prior art pet collars, the collar may include a processor and may interpret the interdependence of the vital sign measurements made by the sensor array to arrive at a tentative diagnosis that may be relayed to a veterinarian, the pet owner and/or to the authorities. In further contrast to prior art methods and appartuses of monitoring the pet animals' vital signs, which may interfere with the pet animal's behavior, for example because the collar has to be too tight, or which may not be sufficiently effective in capturing the low frequency sounds made by the animal, due to the fur of the animal around the neck of the animal, the collar and method of the present invention may provide an effective method of monitoring the vital signs and diagnosing the health condition of the pet animal accurately without adversely affecting the behavior or comfort of the animal. Despite its accuracy, the collar may only need to gently touch the animal's neck, for example through its fur, at several points around the neck. In still further contrast to the prior art animal pet collars, such as dog collars, in which signal to noise ratio precludes remote telecommunication reception of vital sign parameters, the collar of the present invention may include a layer of elastic material that may improve the sentivitiy, gain and signal to noise ratio by absorbing friction from constant movement of the dog or pet's head. In still further contrast to the prior art collars, which may not be accuaarate in capturing the low frequency sounds made by the animal, the collar and method of the present invention may utilize an acoustically enhanced collar whose band for positioning on a neck of the pet animal may have a working surface and a rear surface, at least two acoustic concentrators projecting toward a neck of the pet animal from the working surface on one side of the at least one sensor element and at least two acoustic balancers projecting from the rear surface on the other side of the at least one sensor. An acoustic balancer may be positioned at least partly behind a corresponding acoustic concentrator, and in some preferred embodiments the positioning maybe such that most or all of the acoustic concentrators have an acoustic balancer at least partly behind it on opposite sides of the band. In further contrast to prior art collars, in which the structure of the device does not optimize capturing the low frequency sound by creating a balanced acoustic signal that is readable and able to be parsed, the collar of the present invention may have enhanced ability to convert low mechanical pulses to electrical signals of reasonable magnitude for transmission to the processor and thereby capture the low frequency sound effectively as a balanced acoustic signal that is readable and able to be parsed. Furthermore, in contrast to the prior art, the acoustic enhancers (concentrators and balancers) of the collar of the present invention may perform this function while simultaneously reducing total noise by reducing relative movement between the collar and the pet animal's head when the pet animal's head moves. The acoustic concentrators in the form of bumps may prevent occasional rotation of the collar relative to the neck of the animal. Instead, the collar of the present invention may move with the animal's head when the animal turns its head due to the inward facing acoustic concentrators. Keeping the collar at the desired place may be critical both for the accuracy of the acoustic sensor and for the accuracy of the acceleration/position sensor that may be on the collar. In further contrast to prior art sensor devices on collars, the structure each of the at least one acoustic concentrator may be wider at a concentrator base end adjacent the working surface than at a concentrator top end, and each of the acoustic balancers may be wider at a balancer base end adjacent the rear surface than at a balancer top end. In further contrast to the prior art, the collar may include substantially semispherical acoustic concentrators and acoustic balancers. In contrast to the prior art structure of collars, in some preferred embodiments of the present invention, the acoustic concentrators and acoustic balancers, which may comprise bumps that may be integrally formed with the band and that are made of the same material as the band, may comprise X-shaped concentrator base ends and balancer base ends, and/or X-shaped cross-sections, which may include perpendicular diameters. For example each concentrator base end of at least one acoustic concentrator of the at least two acoustic concentrators may have a cross-section shaped like an X inside a substantially closed curve and in some preferred embodiments each balancer base end of the at least two acoustic balancers may comprise an X-shape inside a substantially closed curve. The cross-section of an acoustic balancer may be shaped like an X inside a substantially closed curve. In some other preferred embodiments, the acoustic concentrators and acoustic balancers are solid and not hollow. In still further contrast to the prior art structure, the acoustic concentrators and acoustic balancers have a diameter of between 5 and 7 millimeters in some preferred embodiments. In further contrast to the prior art, the collar may have two-way communication so that a veterinarian can instruct the collar to measure a particular vital sign remotely. In addition, the collar of the present invention may also have a GPS and communications system for alerting remote personnel so that if ithe pet animal is ill, or if a captive animal in a zoo escapes its enclosure, an immediate alarm can be sounded and an alert transmitted to deisgnated authorities and veterinarians. In contrast to prior art methods and apparatuses of monitoring vital signs which are sometimes invasive, the present invention may involve a non-invasive apparatus that may be worn on the anaiml's collar. In contrast to prior art collars, which may monitor vital signs but which may not simultaneously alert health practitioners/authorities and assist in diagnosing the health condition of the pet animal, the collar of the present invention may be effective to accomplishing both in a single device.

The principles and operation of a method and apparatus for an acoustically enhanced pet animal collar for health & vital signs monitoring, alert and diagnosis may be better understood with reference to the drawings and the accompanying description.

Figure 1:
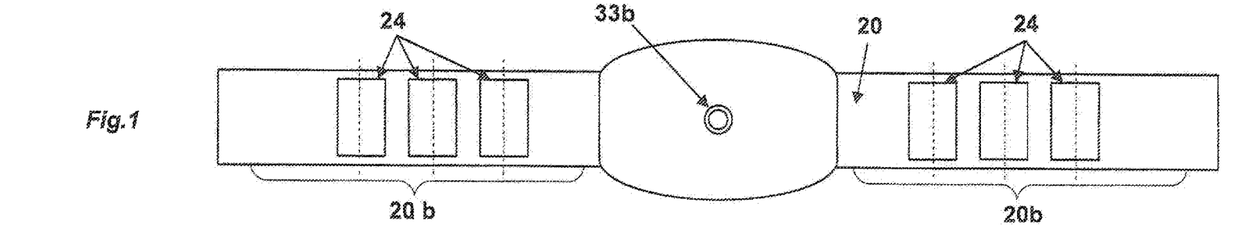
FIG. 1 is a top view of an opened collar, in accordance with one embodiment of the present invention.
Figure 2:
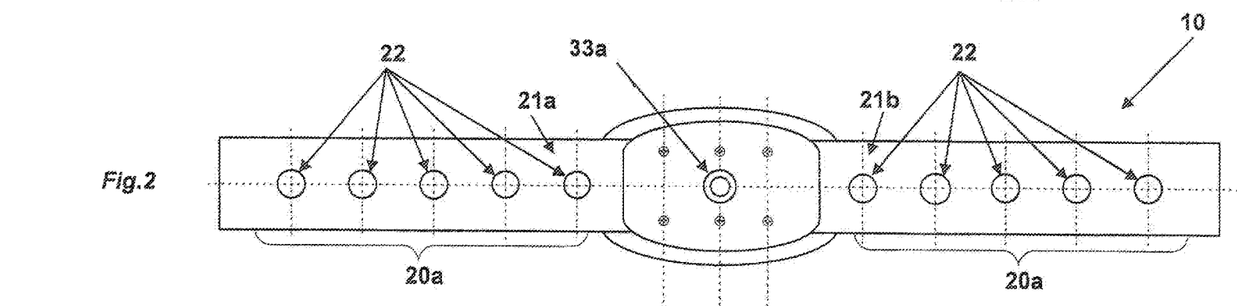
FIG. 2 is a bottom view of the collar of FIG. 1, in accordance with one embodiment of the present invention.
Figure 3:
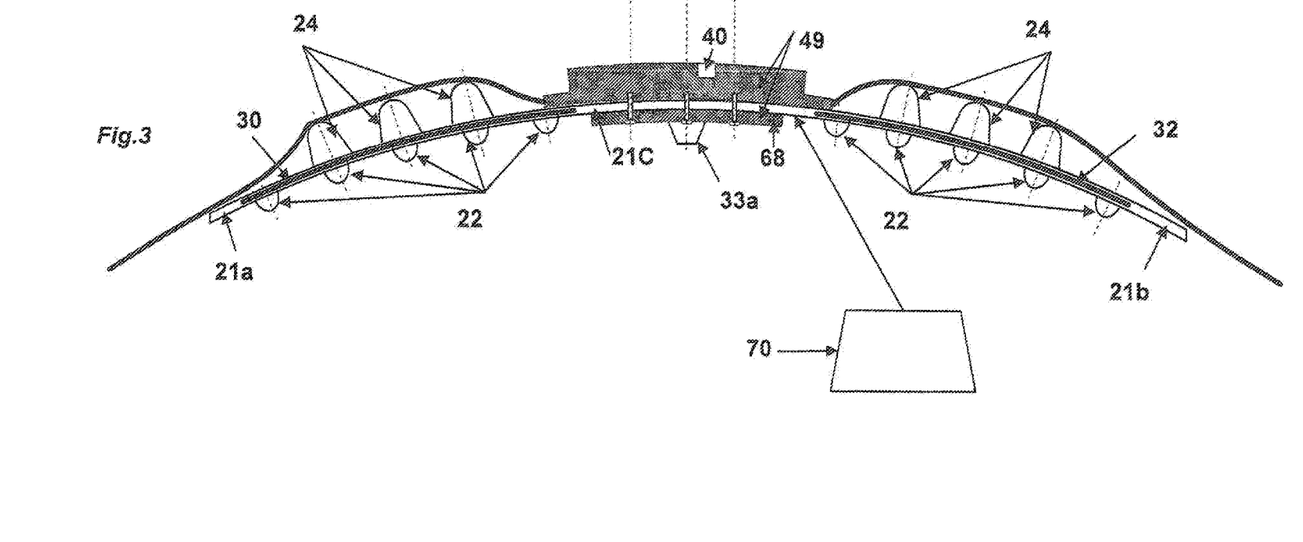
FIG. 3 is a longitudinal sectional view of an opened collar, in accordance with one embodiment of the present invention.
Figure 3A:
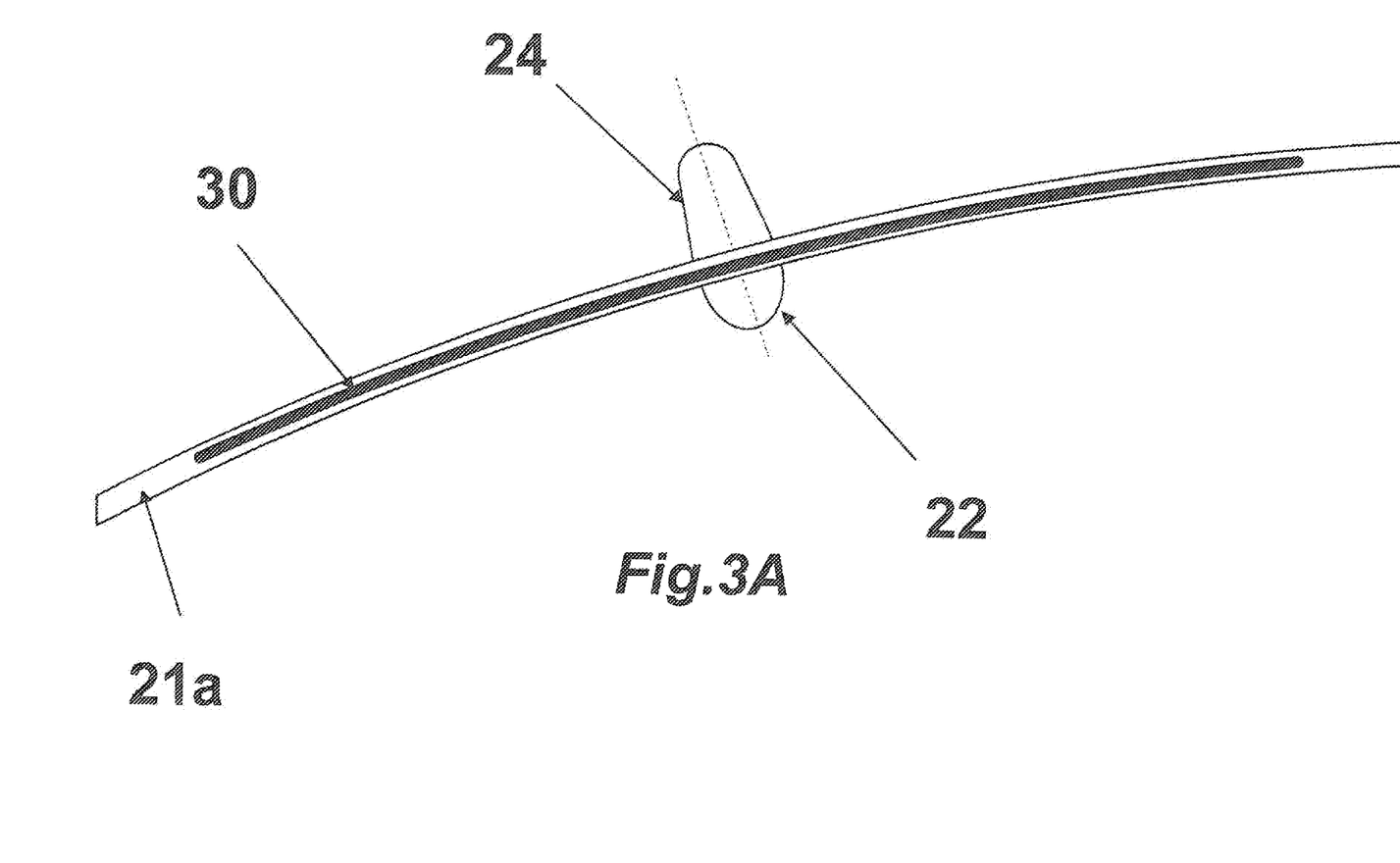
FIG. 3A is an enlarged sectional view of a portion along the circumference of the collar showing a piezoelectric element inside the band, in accordance with one embodiment of the present invention.

As seen from FIGS. 1-3, the present invention may be described as an acoustically enhanced collar 10 for monitoring vital signs of a pet animal. Collar 10 may include a band 20 that may comprise a layer of an elastic material, for example polyurethane. The elastic material may include any kind of plastic or other flexible material, although in a preferred embodiment, elastic material may comprise polyurethane. The band 20 may be configured for cushioning repetitive instances of friction against the collar 10 from movement of the head of the pet animal. Although the remainder of this application may refer primarily to the "neck" of the pet animal, it should be understood that other portions of the animal may also hold the collar.

Band 20 may have a working surface 20a that may be configured to wrap around a portion of a pet animal, for example a neck of the animal which may be a dog, and may have a rear surface 20b that may face an opposite direction from working surface 20a. For example, working surface 20a may face the animal's neck and rear surface 20b may face a viewer looking directly at the band 20 of the collar 10 on the neck of the animal. Band 20 (and collar 10) may be approximately two inches wide and may cover an entire circumference of the neck of the pet (or alternatively most or a portion of this circumference). There may be sensors 30, for example four or more sensor elements 30 at different points of the band, preferably at different points along a length or circumference of band 20. There may be other numbers of sensor elements, such as one, two, three, five, six, seven, eight, nine or ten and more.

Figure 4A:
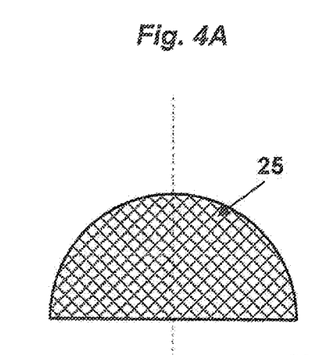
FIG. 4A is a vertical sectional view of a cross-shaped acoustic concentrator, in accordance with one embodiment of the present invention.
Figure 4B:
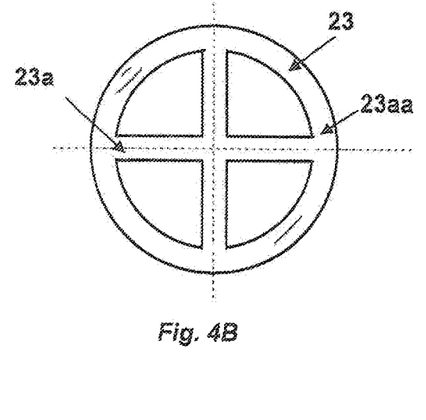
FIG. 4B is a bottom view of the acoustic concentrator of FIG. 4A, in accordance with one embodiment of the present invention.
Figure 5A:
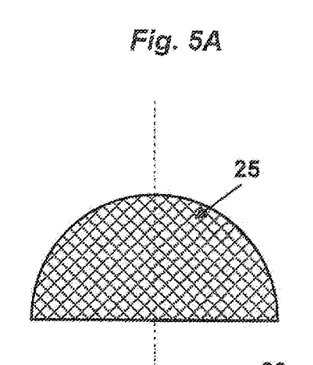
FIG. 5A is a vertical sectional view of a solid acoustic concentrator, in accordance with one embodiment of the present invention.
Figure 5B:
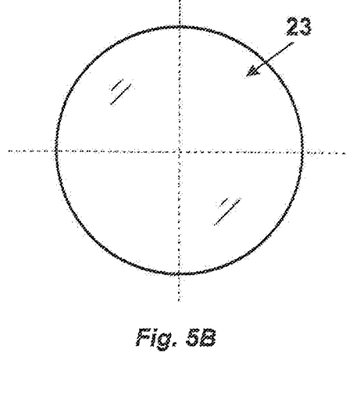
FIG. 5B is a bottom view of the acoustic concentrator of FIG. 5A, in accordance with one embodiment of the present invention.
Figure 6A:
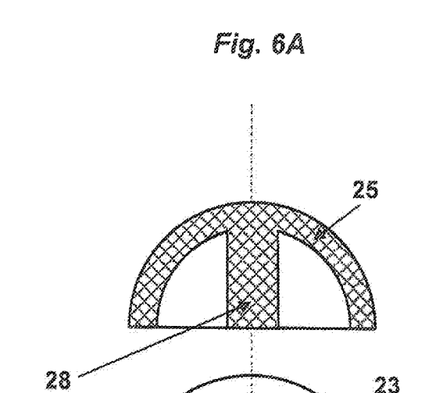
FIG. 6A is a vertical sectional view of a dot shaped acoustic concentrator, in accordance with one embodiment of the present invention.
Figure 6B:
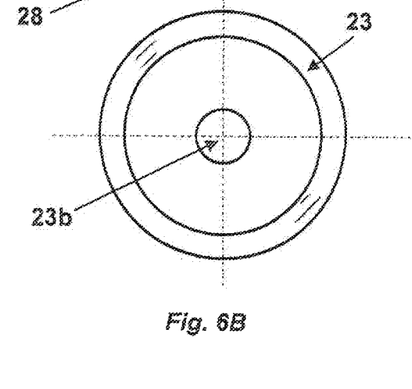
FIG. 6B is a bottom view of the acoustic concentrator of FIG. 6A, in accordance with one embodiment of the present invention.

Each acoustic concentrator 22 may have a concentrator base end 23, which refers to the base of the acoustic concentrator adjacent the working surface 22a, (see FIGS. 4B, 5B, 6B). Each acoustic concentrator 22 may have a concentrator top end 25 (see FIGS. 4A, 5A, 6A), the end projecting furthest from the band 20 and closest to the animal's neck, for example. Likewise, each acoustic balancer 24 may have a balancer base end 27 (see FIGS. 7B, 8B, 9B) and a balancer top end 29 (see FIGS. 7A, 8A, 9A).

In a preferred embodiment, in which we consider an acoustic concentrator 22 and an acoustic balancer 24 to constitute a "pair" as shown for example in FIG. 3, there are at least two pairs of acoustic concentrators 22 and acoustic balancers 24 for each sensor element 30, 32. The at least one sensor element 30 (on the left side of the band 20) and the at least one sensor element 32 on the right side of band 20 may each comprise a piezoelectric material which in a preferred embodiment may be embedded inside band 20.

If there are two sensors elements, then the sensors 30 may be connected in parallel electrically (the at least one sensor element 30 may comprise two physically separated sensors connected electrically). One can also define the two sensor elements 30 as one distributed sensor element. Positioning two sensors 30 on the two sides of the neck of the animal may provide a guaranteed contact with the body regardless of movement or position.

As shown in FIGS. 1-3, collar 10 may have at least one acoustic concentrator 22 projecting from the band 20 towards the neck (not shown) of the pet animal (not shown). The acoustic concentrator 22 may touch the skin of the pet and absorb the noise from friction while conducting the signal and may penetrate the fur on the neck of the animal without causing the animal discomfort. This may be arranged by configuring the height of the projection (its length from the sensor element 30 substantially perpendicularly toward the neck of the pet animal) and thereby controlling how far the acoustic concentrator projects toward the direction of the neck of the pet animal. The comfort of the pet animal may be verified by testing the collar on various pet animals of the particular species.

In one preferred embodiment, as shown in FIGS. 1-3, collar 10 may include at least one sensor element 30 situated at one or more regions along a circumference of the band 20 and configured to measure at least one bioparameter relating to vital signs of the animal. The term "region" is not intended to indicate how much length the region has and the region can be as long as the band 20 or as narrow as a line, although as shown in FIG. 3, it is preferably elongated along a circumference of the band 20. In a preferred embodiment, the at least one sensor element may be configured to measure at least one bioparameter from the following bioparameters: temperature, heart rate, respiration rate, movement. Preferably, the at least one sensor element is configured to measure at least two of the bioparameters, and more preferably at least three and most preferably all four of them.

In one preferred embodiment, collar 10 may have at least two acoustic concentrators 22, projecting toward a neck or other portion of the pet animal from the working surface 20a at the one or more regions along the circumference of the band 20 that the at least one sensor element may be situated in. Likewise, collar 10 may have at least two acoustic balancers 24 projecting from the rear surface 20b at the one or more regions along the circumference of band 20 that the at least one sensor element may be situated in. As seen from FIG. 3, the at least two acoustic balancers 24 may be situated at a region along the circumference of the band 20 that is at least partly behind the at least two acoustic concentrators the at least one sensor 30, the at least two acoustic balancers situated opposite the at least two acoustic concentrators. Preferably, the at least two acoustic concentrators and the at least two acoustic balancers are situated so that one acoustic concentrator is directly opposite one corresponding acoustic balancer, as shown in FIG. 3. In some preferred embodiments, as shown in FIG. 3, the base end 23 of at least one acoustic balancer 24 is at least as wide as the base end 27 of the acoustic concentrator 22 that it is behind. More preferably, the one acoustic concentrator that is opposite its corresponding one acoustic balancer is of the same or similar shape as the corresponding one acoustic balancer. This may mean that a pair comprising one acoustic concentrator 22 and one acoustic balancer 24 at least partly behind it have the same overall shape, but in other preferred embodiments, it may mean that they have the same width, or that they have the same cross-section or the same shape at their base end 23 (the end facing the band 20) or the same width at their base end, or both have perpendicular diameters at their base ends or other structural similarities.

Another preferred embodiment of the present invention may comprise an acoustically enhanced collar for monitoring vital signs of a pet animal comprising a band 20, for example annular band 20, comprising a layer of an elastic material, the band having a working surface 20a configured to wrap around a portion of a pet animal (such as a neck) and an oppositely faced rear surface 20b. The neck is a particularly suitable portion of the pet animal to monitor since it not only allows listening acoustically to two major blood vessels (arteries) but also monitoring a breathing pipe (the windpipe).

As shown in FIGS. 1-2, band 20 may have a first side 21a and a second side 21b along its circumference. These "sides" may be portions of the circumference of band 20, for example on each side of a centrally located sensor element 33 (FIG. 3) (for example a temperature sensor 33a for measuring body temperature as shown in FIG. 2 and a temperature sensor 33b for measuring ambient temperature as shown in FIG. 1) and these "sides" should not be confused with the "vertically" opposite sides (working surface and rear surface) of or in relation to a sensor element 30 that the acoustic concentrators 22 and acoustic balancers 24 may be on. The first side 21a along the circumference of the band 20 may be on the left side of the neck of the animal and the second side 21b along the circumference of the band 20 may be the right side of the neck of the animal or vice versa. This may allow a most preferable embodiment in which at least one sensor element is positioned on the first side of the neck and at least one sensor element is positioned on the second side of the neck. FIG. 3 also shows a central portion 21c of the circumference of band 20 that may be located between sides 21a, 21b.

At least one sensor element 30 may be situated at one or more regions along a circumference of the band 20, and the at least one sensor element 30 may be configured to measure at least one bioparameter from the following bioparameters: temperature, heart rate, respiration rate, movement. As shown in FIG. 1 and FIG. 3, collar 10 may also include at least one acoustic concentrator 22 projecting as a bump toward the portion of the animal (for example the neck) from the working surface 20a. The at least one acoustic concentrator 22 may be situated at the one or more regions along the circumference and on a first vertical side (vertically speaking by reference to FIG. 3) of the at least one sensor element 30 that may be embedded in the band 20 (see FIG. 3). As also seen from FIGS. 2-3, at least one acoustic balancer 24 may be situated along the one or more regions of the circumference and may be projecting as a bump from the rear surface 20b of the band 20 on a second vertical side of the at least one sensor element. The position of the at least one acoustic balancer along the circumference of the band may be that it is at least partly behind, and preferably directly behind, the at least one acoustic concentrator 22.

As also shown in FIG. 3, a similar arrangement may exist on the other side 21b of the circumference of the band 20 with another at least one sensor 30 and another at least one acoustic concentrator 22 and another at least one acoustic balancer 24 similarly configured for example behind, and preferably directly behind, the at least one acoustic concentrator 22. This may allow monitoring both sides of the neck of the animal.

One or two or preferably all of the at least one acoustic concentrator 22 are wider at a concentrator base end 23 adjacent the working surface 20a than at a concentrator top end 25. One or two or preferably all of the at least one acoustic balancers 24 are wider at a balancer base end 27 adjacent the rear surface 20b than at a balancer top end 29. In one preferred embodiment shown in FIGS. 4A-6B, the at least one acoustic concentrator 22 and the at least one acoustic balancer 24 are substantially circular in at least one dimension. An acoustic concentrator 22 of the at least one acoustic concentrator may be substantially semispherical. An acoustic balancer of the least one acoustic balancer may be substantially semispherical and may be located at least partly behind, and preferably directly behind, the acoustic balancer of the at least one acoustic concentrator on the first side 21a that is substantially semispherical. In other embodiments, the least one acoustic concentrator may be substantially semi-cylindrical (not shown) and the at least one acoustic balancer may be substantially semi-cylindrical (not shown) and located at least partly behind and preferably directly behind the one of the at least one acoustic concentrators that is substantially semispherical.

In a preferred embodiment of the structure of the bumps comprising the acoustic concentrators 22 shown in FIGS. 4A-4B, each concentrator base end 23 of the at least one acoustic concentrator 22 may comprise an X-shape and may have perpendicular diameters. For example, the concentrator base end 23 of at least one acoustic concentrator may comprise an X-shape 23a inside a substantially closed curve. In a preferred embodiment of the structure of the bumps comprising the acoustic balancers 24 shown in FIGS. 7A-7B, each balancer base end 27 of the at least one acoustic balancer 24 may comprise an X-shape and may have perpendicular diameters. For example, the balancer base end 27 of at least one acoustic balancer 24 may comprise an X-shape inside a substantially closed curve. Although the examples in FIGS. 7A-9B appear identical to those of FIGS. 4A-6B, this does not preclude the acoustic balancers 24 from being of a different size for example wider, than the acoustic concentrators 22, as shown in FIG. 3.

It should be understood that references to an "X-shape" or "X" in this patent application include such shapes whether the lines of the "X" meet at right angles or at smaller or larger angles. A most preferred embodiment of the X-shape in this patent application is where the lines of the "X" meet at perpendicular angles or substantially perpendicular angles (80 to 100 degrees).

In a different embodiment shown in FIG. 6A-6B, each concentrator base end 23 of the at least one acoustic concentrator 22 may comprise a central dot 23b connected to the concentrator top end along a linear axis 28.

The acoustic concentrators 22 may be designed to optimize the acoustic transmission of sound vibrations from the pet animal's neck to the sensor element 30 in the band 20. In order to accomplish their purpose, the acoustic concentrators 22 and acoustic balancers 24 of the collar 10 may vary in terms of their size and in terms of their shape. With regard to their shape, an important aspect of their shape is the configuration of the base end of the acoustic concentrator or balancer. The base end of the acoustic concentrator (concentrator base end) and the base end of the acoustic balancer (balancer base end) are each closer to the sensor element 30 than the respective top ends (concentrator top end and balancer top end).

As shown in FIGS. 3, 4A, 5A, 6A, one or two or preferably all of the at least two acoustic concentrators 22 may be wider at a concentrator base end 23 adjacent the working surface 20a than at a concentrator top end 25. Likewise, as shown in FIGS. 3, 7A, 8A, 9A, one or preferably each of the at least two acoustic balancers 24 may be wider at a balancer base end 27 adjacent the rear surface 20b than at a balancer top end 29. The term "projecting" refers to the fact that the acoustic concentrators 22 and balancers 24 may project beyond the surface of the band 20, which may be relatively flat other than the acoustic concentrators and balancers. Although, these projections have been referred to as "bumps", the term "bump" is not intended as a limitation on the shape of the projections, although in many preferred embodiments, the "bumps" look like curved protrusions akin to a bump. In certain preferred embodiments, the acoustic concentrators 22 and acoustic balancers 24 are rounded and symmetrical.

Preferably, there are at least four sensor elements 30. Each sensor element 30 may be a strip of two inches to six inches in length depending on the size of the collar 10. In a preferred embodiment, there are at least two acoustic concentrators for each sensor element. For example, in one preferred embodiment where the sensor element is two and three-quarters inches, there may be four acoustic concentrators for that sensor 30. Acoustic concentrators 22 and acoustic balancers 24 may be located at the opposite sides of the sensor, as shown in FIG. 1 and FIG. 3. The collar 10 contains two sensors located symmetrically at the left and right sides of the neck. The acoustic concentrators and the acoustic balancers may be integrally formed with the band and may be made of the same material as the band. For example, the bumps (acoustic concentrators and acoustic balancers) may be formed at the same time that the band is formed. Preferably, each of the at least two acoustic concentrators 22 are shaped like a bump, for example like a bump that diminishes in diameter from the concentrator base end to the concentrator top end. Likewise, preferably, each of the acoustic balancers are shaped like a bump, for example like a bump that diminishes in diameter from the balancer base end to the balancer top end. The bumps, in a preferred embodiment, may be mostly hollow except for particular structural elements in particular shapes that may fill the void of the hollow.

The acoustic concentrators 22 (or one particular acoustic concentrator of the at least one acoustic concentrator) and the acoustic balancers 24 (or one particular acoustic balancer of the at least one acoustic balancer) may be mathematically elliptical, for example substantially circular, in at least one dimension. Preferably, they may be substantially circular in two dimensions. As shown in FIGS. 2, 3, 4B, 5B, 6B, at least one, and preferably at least two, of the acoustic concentrators are substantially semispherical. Preferably, the shape of an acoustic balancer 24 mirrors the shape of the acoustic concentrators 22 that the balancer 24 faces on the opposite side of the band 20. Accordingly, preferably, at least one, and preferably at least two, of the at least two acoustic balancers 24 are substantially semispherical. In a different preferred embodiment (not shown), at least one of the at least two acoustic concentrators 22 is substantially semi-cylindrical and at least one of the at least two acoustic balancers 24 may also be substantially semi-cylindrical in this embodiment.

Figure 9A:
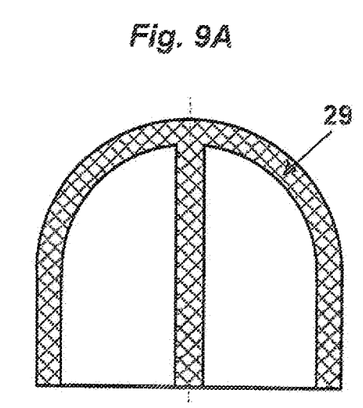
FIG. 9A is a vertical sectional view of a dot shaped acoustic balancer, in accordance with one embodiment of the present invention.
Figure 9B:
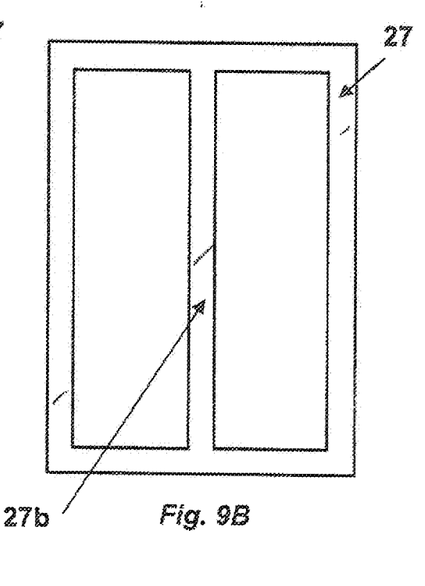
FIG. 9B is a bottom view of the acoustic balancer of FIG. 9A, in accordance with one embodiment of the present invention.

As shown in FIG. 6A-6B, each concentrator base end of the at least one or the at least two acoustic concentrators 22 may comprise a central dot 23b connected to the concentrator top end 25 along a linear axis 28. As shown in FIGS. 9A-9B, each balancer base end 27 of the at least one or the at least two acoustic balancers 24 may comprise a central dot 23b connected to a balancer top end 29 along a linear axle 28. In this embodiment, as shown in FIGS. 6A-6B and 9A-9B each acoustic concentrator 22 and each acoustic balancer 24 may be hollow except for the central dot and linear axle.

Figure 7A:
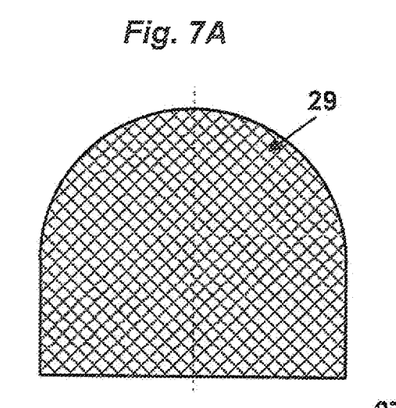
FIG. 7A is a vertical sectional view of a cross-shaped acoustic balancer, in accordance with one embodiment of the present invention.
Figure 7B:
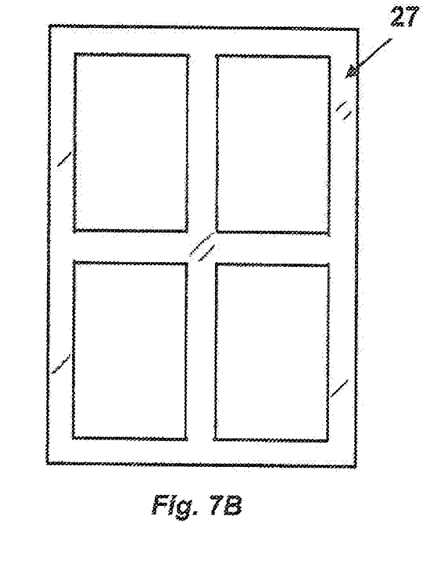
FIG. 7B is a bottom view of the acoustic balancer of FIG. 7A, in accordance with one embodiment of the present invention.

In the preferred embodiment of the concentrator base end 23 and the balancer base end 27, shown respectively in FIG. 4B and FIG. 7B, the X-shape 23a or perpendicular diameters may appear in a closed curve or a substantially closed curve. The "closed curve" may be a circular perimeter. As shown in FIG. 4B and FIG. 7B, the circular perimeter 23aa of the X-shape may be thicker than a thin outer perimeter and could in some preferred embodiments be thick enough to occupy 10% to 20% of the diameter/width of the concentrator base end 23 or of the balancer base end 29 (and in certain other preferred embodiments 5% to 10% or 15% to 30% or 3% to 6% or about 3% or about 5%, or about 10%, or about 15%, or about 20%, or about 25% or about 30% or other numbers depending on the embodiment of the diameter/width of the concentrator base end 23 or of the balancer base end 29). This proportion presupposes that the thickness of the perimeter is included in the calculation only once (not twice due to the two parts of the perimeter appearing 180 degrees apart from on another). As shown in FIG. 4A and FIG. 7A, the cross-section of the acoustic concentrators 22 and the acoustic balancers 24 may in the shape of an "X".

Figure 8A:
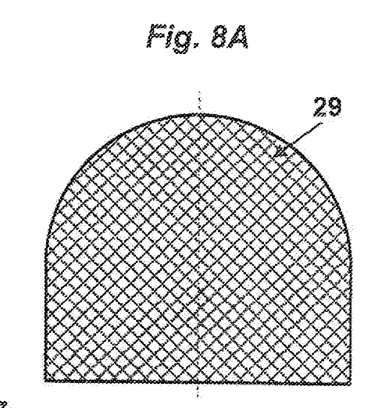
FIG. 8A is a vertical sectional view of a solid acoustic balancer, in accordance with one embodiment of the present invention.
Figure 8B:
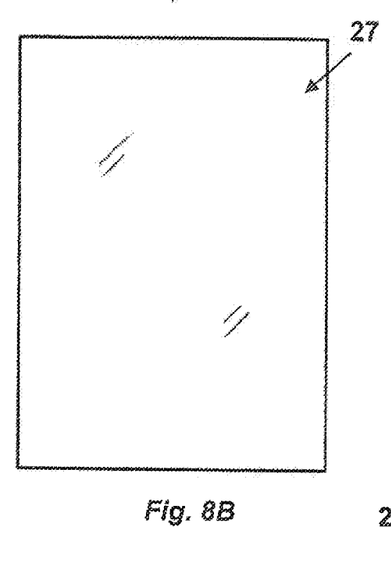
FIG. 8B is a bottom view of the acoustic balancer of FIG. 8A, in accordance with one embodiment of the present invention.

In certain other preferred embodiments, the acoustic concentrators and acoustic balancers are solid, as shown in FIG. 5B and FIG. 8B.

Depending on the shape, the bumps comprising the acoustic concentrators and acoustic balancers may have a diameter of between 5 and 7 millimeters. Depending on the shape, the acoustic concentrators and acoustic balancers may also have a height of between 5 and 7 millimeters.

As a result of the acoustic concentrators and acoustic balancers, the signal to noise ratio expressed using the logarithmic decibel scale may be at least 20 dB and in some preferred embodiments between 20 dB and 40 dB. The typical pulse amplitude is between 300 and 500 mV, as defined by the gain setting of the amplifier (not shown).

In general, sensor elements 30 may be at least one sensor element 30 designed or configured to measure at least one bioparameter from among temperature, heart rate, respiration rate and movement. Alternatively, the sensor element may be for measured a different vital sign. There could be more sensor elements and more bioparameters. For example, the at least one sensor element 30 may comprise at least two sensor elements 30 that may be configured or designed to measure at least two bioparameters from among temperature, heart rate, respiration and movement. Alternatively, the at least two sensor elements 30 may be for measuring at least two bioparameters from among temperature, heart rate, respiration rate and movement (or alternatively other vital signs). One sensor element may measure multiple bioparameters, for example, in the case of an acoustic sensor that measures respiration rate and heart rate. The at least two sensor elements may comprise four or more sensor elements designed to measure four or more bioparameters or specifically those four: temperature, heart rate, respiration rate and movement. In some preferred embodiments, the array of sensor elements 30 are designed to measure one or two bioparameters (in other preferred embodiments three or four) from the following bioparameters: temperature, heart rate, respiration rate, movement (for example horizontal and vertical movement).

The sensor elements 30 may be designed or configured to measure at least two different vital sign bioparameters as well as to measure certain bioparameters, such as movement, that may be useful in understanding a pet's vital signs when combined with other vital sign bioparameters. Each of the various sensor elements 30 on the band 20 may be designed for measuring a different vital sign parameter or in some cases there may be more than one sensor element measuring a particular vital sign bioparameter or more than one vital sign measured by a particular sensor element 30.

A sensor array (not shown) may include an acoustic sensor element for measuring pulse (heart rate) and an acoustic sensor for measuring respiration rate. Such a sensor array may include an accelerometer to measure movement and vibrations of air traveling through the pet's air canals during inhaling and exhaling motions as well as the movement of blood traveling through the main blood vessels across the pet's neck. A sensor array may also include a temperature sensor to measure the temperature of the pet's body and an ambient temperature sensor to measure the ambient temperature.

A sensor array may also include a microphone 30c. A sensor array may further include a microphone to listen to special noises made by a pet animal, for example a dog. In the case of a dog, there are about twenty-six separate sounds that they normally make. These include the following: barking sounds (including guarding/warning bark, alarm barking, playing, anxiety, need bark), yelping, growling, howling, eating, drinking, breathing (including normal breathing through the nose (inspiration and expiration), open-mouthed breathing, dry cough, wet cough, stertor, stridor, laryngeal paralysis, wheezing, rales/crackles, bronchio-vesicular sounds), vomiting/retching, regurgitation, grunting, groaning, and panting. Furthermore, each of these types of sounds may be further subdivided into sounds of those type made by a small dog, made by a large dog, made by a deep-chested dog and made by a puppy dog. Accordingly, the sounds picked up by a microphone may be interpreted by a processor 40 having an associated memory storage 67 (FIG. 3) of collar 10 or a remote processor of a remote computer terminonal 69 (FIG. 4) and/or by a processor having access to a dedicated or remote database to determine the type of sound and its interdependence with other vital sign bioparameters in order to arrive at a tentative diagnosis, to determine whether an alert is justified or to suggest treatment.

The sensor array 30 may also include a gyroscope 30d for capturing the vertical and/or horizontal movement of the pet. In the case of dogs, there are numerous basic dog postures that provide information as to what the dog is doing and thereby assist in interpreting vital sign measurements to arrive at a tentative diagnosis. The following basic dog postures that may be detected by sensor elements 30, for example a gyroscope, an accelerometer and/or a magnetometer: lying down laterally, lying down sternally (head up/down), lying on back, sitting, standing on four legs, standing on back legs, jumping, trotting, running, eating/drinking, urinating (male/female), defecating, limping hind leg, limping front leg, scratching hind leg, shaking leg, turning to lick, and stretching. The processor 40 make receive this information from the sensors 30 and utilize it in reaching a conclusion that it transmits remotely to the appropriate destination.

Each of the sensors 30 may be activated, de-activated, fine-tuned, set for predetermined repeated intervals or otherwise calibrated or controlled remotely, and in some embodiments also manually by a person located at the collar 10. "Remotely" means remote from the collar 10 and may include by a person in a vital sign monitoring station or a remotely stationed veterinarian or a medical center or the pet owner or the authorities or any other suitable location.

Collar 10 may further include a remotely-actuatable speaker (not shown) for communicating sounds to the pet animal remotely and may include a remotely actuatable light (such as an LED or other light source) for illuminating the pet animal to those seeking to locate it. The speaker and light may also be actuatable manually in person. The speaker and light may be situated on or attached to the band 20 and may be included in a sensor array (even though the light is not a sensor).

As seen from FIG. 3, collar 10 may also include a controller 49 that includes a processor 40 that may be affixed to the collar 10 for example in a housing (not shown) attached to the collar 10. As shown in FIG. 3, processor 40 may also include a processing unit having MicroElectro Mechanical Systems ("MEMS") technology. As also shown from FIG. 3, processor 40 may be hard-wired or otherwise in electronic communication with each of the sensor elements 30. Processor 40 may be configured to receive a signal representing data sensed by one or more of the sensor elements 30 and may be configured to analyze the data and communicate vital sign determinations and other data to a telecommunications system. The vital sign data measured by the sensor elements 30 of collar 10 may be relayed to and interpreted by processor 40 or by a remote processor (not shown). Processor 40 or the remote processor may execute algorithms to interpret a collection of the physiological data sensed by the sensor elements and the interdependence of the vital sign data from the sensor elements and may arrive at a tentative diagnosis. The vital sign data may also include physiological data such as data about the movement of the pet animal (or other physiological data such as the saltiness of the animal's skin) since this physiological data, when combined with fundamental vital signs such as breathing rate, respiration rate, pulse, temperature, etc. may be useful in diagnosis by the veterinarian or remote computer server for the automatic temperoray diagnosis by the processor 40.

Controller 49 may also include a memory storage 67 for storing health information history of the pet animal, the memory storage accessible by the processor 40. The memory storage can be a flash memory or other memory storage devices known in the art.

As shwn in FIG. 3, collar 10 may include a communication device 68 such as a wireless transmitter unit, that may be accompanied by a receiving unit 68a forming a two-way communicaiton device for communication to a remote station which may include a computer server pre-programmed to interact with the processor 40 or the remote station may communication with or include a veterinarian who can remotely measure vital signs using the collar's processor to select particular sensor elements to be activated to measure vital signs of the pet. As shown in FIG. 3, there is an onption for there to be a remote station 70 (which may be a remote computer server) which may also alert a pet owner or the authorities by sending an email communication or an SMS alert. The communication device may also incorporate short range or long range wireless communication technology such as UHF, Wi-Fi, Bluetooth, etc. and cellular technology.

The collar 10 and/or server computer or other part of the system may issue an alert based on predefined parameters (e.g. unique prior knowledge regarding the specific animal) and/or behavioral (e.g. erratic or uncharacteristic movements) or vital signs parameters. The specific measurements of the animal (height, length, weight etc.) and relevant history may be loaded into the device and/or the system during a registration procedure. The unique identification data of the animal can also include: the pet animal's name, owner's names, personal details (address, phone number etc.), medical information concerning the pet and any other relevant data. The information may be included in the processing by processor 40 when the processor 40 analyzes data from the sensor elements 30.

A GPS device may be incorporated into collar 10. The GPS device could take the form, for example, of an integrated circuit or an RFID. Other location awareness technology may also be incorporated into the collar 10.

The receiving unit 68 attached to or incorporated into the collar 10 may be a smart phone, mobile (and/or hand-held) device, or any other communication/messaging device, or a specifically designed receiver or reader. The receiving unit 68 may be connected to the collar 10 in a wired and/or wireless manner as mentioned above. The receiving unit 68 may be detachable from the collar 10 for direct connection to a computer terminal, in order to enable faster or more secure downloading of stored (and in some cases processed) sensor data.

The collar 10 and/or system may gather analytical information including statistics, trend analysis, comparative analysis etc. regarding particular pets, particular breeds of pets or particular species of animals. The system may incorporate a social network for other animal owners for the purpose of sharing information.

Figure 10:
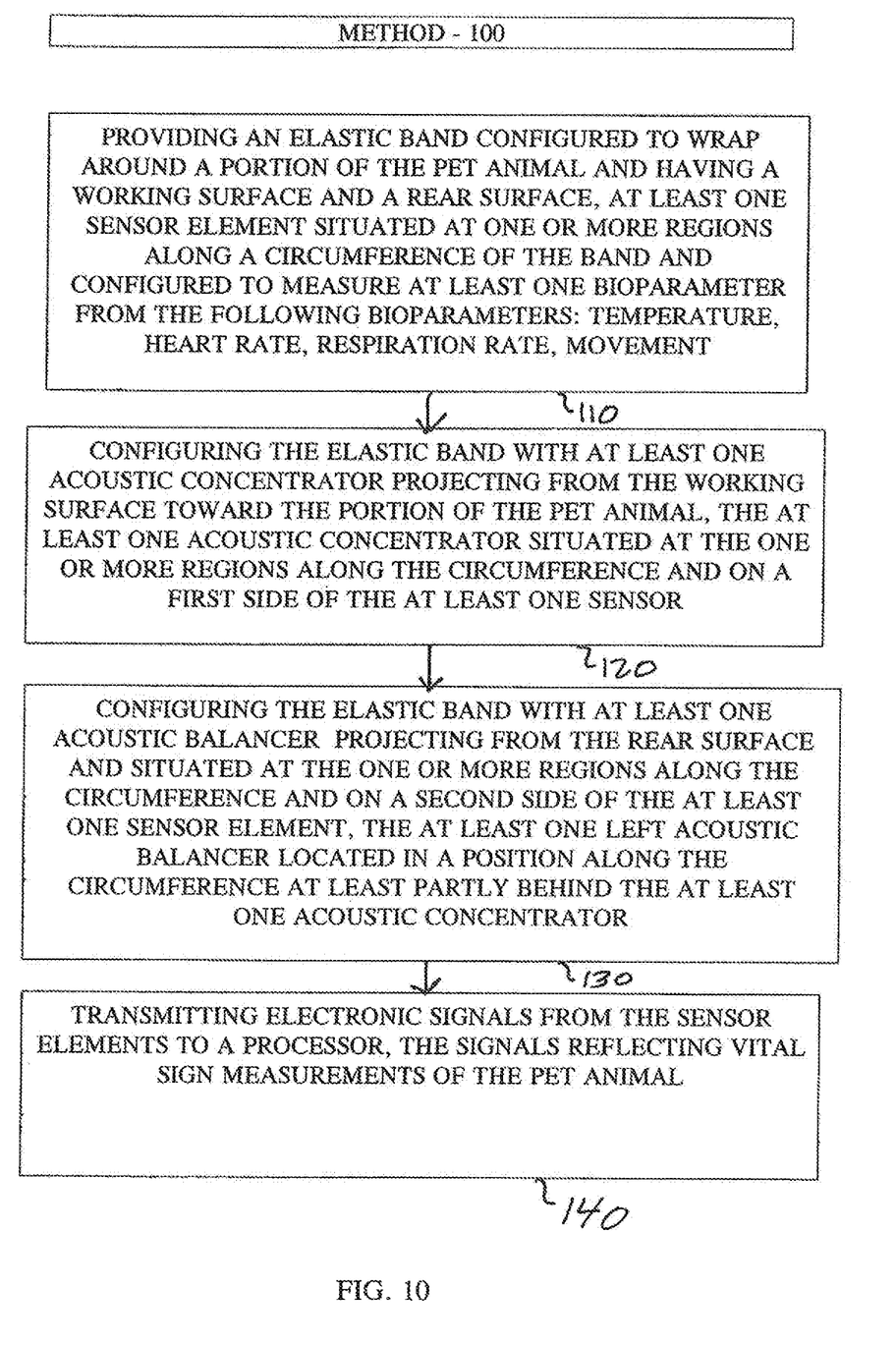
FIG. 10 is a flow chart showing a method, in accordance with one embodiment of the present invention.

As shown in FIG. 10, the present invention may also be described as a method 100 of monitoring vital signs of a pet animal. Method 100 may include a step 110 of providing an elastic band configured to wrap around a portion of the pet animal and having a working surface and a rear surface, at least one sensor element situated at one or more regions along a circumference of the band and configured to measure at least one bioparameter from the following bioparameters: temperature, heart rate, respiration rate, movement. Another step 120 of method 100 may be configuring the elastic band with at least one acoustic concentrator projecting from the working surface toward the portion of the pet animal, the at least one acoustic concentrator situated at the one or more regions along the circumference and on a first side of the at least one sensor.

Step 130 may involve configuring the elastic band with at least one acoustic balancer projecting from the rear surface and situated at the one or more regions along the circumference and on a second side of the at least one sensor element, the at least one left acoustic balancer located in a position along the circumference at least partly behind the at least one acoustic concentrator.

Step 140 of method 100 may be transmitting electronic signals from the sensor elements to a processor, the signals reflecting vital sign measurements of the pet animal.

Method 100 may also have other steps. The structure of the acoustic concentrators and of the acoustic balancers in method 100 may include any of the options mentioned with respect to the collar 10. For example, in some preferred embodiments, method 100 may have a step of configuring at least one acoustic concentrator to be wider at a concentrator base end adjacent the working surface than at a concentrator top end, and configuring at least one left acoustic balancer to be wider at a balancer base end adjacent the rear surface than at a balancer top end. Some versions of method 100 may also include a step of configuring at least one acoustic concentrator to be semi-spherical. Method 100 may also have a step of configuring a concentrator base end of at least one acoustic concentrator to comprise an X-shape, for example as shown in FIG. 4B with perpendicular diameters. Some preferred embodiments of method 100 may include a step of configuring a balancer base end of at least one acoustic balancer to comprise an X shape, for example as shown in FIG. 7B. Method 10 may also have a step of configuring a cross-section of at least one acoustic concentrator 22 (and/or at least one acoustic balancer 24) to be shaped like an X.

Method 100 can also have a step of configuring the processor that is in electronic communication with the sensor elements to be situated on the collar. There can also be a step of transmitting the signals from the processor on the collar to a remote station. In another embodiment, a step of method 100 may be configuring the processor to be a remote processor that is in electronic communication with the sensor elements.

Method 100 can also include a step of configuring the acoustic concentrators to perform a dual function of simultaneously (i) reducing a signal to noise ratio of the signal transmitted from the sensor elements to the processor and (ii) reducing total noise by reducing relative movement between the collar and the pet animal's head when the pet animal's head moves. In some versions, method 100 can include the step of configuring the at least one acoustic concentrators to perform a dual function of simultaneously (i) improving an ability of the collar to convert low mechanical pulses to electrical signals of reasonable magnitude for transmission to the processor and (ii) reducing total noise by reducing relative movement between the collar and the pet animal's head when the pet animal's head moves.

Method 100 can also comprise having the at least one acoustic concentrators operate in conjunction with the at least one acoustic balancers to improve the ability of the collar to convert the low mechanical pulses to the electrical signals of reasonable magnitude. Further, the method 100 may include conforming a shape of a particular acoustic balancer of the at least one acoustic balancer to a shape of a particular acoustic balancer of the least one acoustic concentrator that the particular acoustic balancer is at least partly behind.

Some versions of method have a step of providing that each acoustic concentrator of the at least two acoustic concentrators has a similar shape to an oppositely placed (one on one vertical side of the least one sensor element on another one the other vertical side of the at least one sensor element) acoustic balancer of the at least two acoustic balancers. Furthermore, method 100 may include situating the at least two acoustic concentrators and the at least two acoustic balancers so that one acoustic concentrator is directly opposite one corresponding acoustic balancer. The preferred position may be having a particular acoustic balancer right behind a particular acoustic concentrator. Other embodiments may have them configured slightly differently such that the acoustic balancer is within a small distance (for example one millimeter (mm) or 2 mm or 3 mm or 4 mm or 5 mm) of the point right behind the acoustic concentrator.

In method 100, the sensors 30 may be placed symmetrically so that at least one sensor is on one side of the neck of the pet animal facing an artery and a matching number of sensors may be on an opposite side of the neck of the pet animal facing an artery. For example, there may be one sensor on one side and one sensor on the other side or two sensors on one side of the animal and two sensors on the other side. The sensors on the opposite sides of the animal maybe connected in parallel electrically so as to form a single distributed sensor.

The method may also include, in some embodiments, a step of transmitting vital sign measurements to the pet owner, a veterinarian, a remote computer server or the authorities when the vital sign measurement exceeds a threshold level. Accordingly, processor 40 may be programmed to compare data received from the sensor elements to threshold levels of respiration rate, heart rate, temperature, movement, blood pressure, and/or other physiological data, such as noises made by a dog. Furthermore, the processor may have access to software in controller 49 that utilizes a function or a formula to relate combinations of the sensor element data. For example, if a dog moves in a certain way and utters a certain noise, that may trigger a particular alert or diagnosis. In addition, the programmer 40 may have access to its own data comparing the physiological data of a particular vital sign or combination of vital signs to the average vital sign data for pets of that species, that breed and that geographical location, taking into consideration the ambient temperature and the medical history of the pet. The controller/processor may transmit an alert to the pet owner, to a veterinarian or to the authorities.

The processor 40 affixed to the collar 10 may be in electronic communication with each of the at least four sensor elements. The processor 40 may control a timing of an "ON" status of each sensor sufficient to trigger taking of a vital sign measurement. The memory storage unit 68 may store data regarding the power requirements of each of the sensor elements in a sensor array (not shown) as well as the lifespan of the battery or other power source in collar 10. Alternatively, this data may be accessible by the processor 40 since processor 40 may be in communication with remote databases. As a result, the processor 40 may be configured to calculate the timing of the "ON" status of a sensor element (or of two or more or all the sensor elements) based on power requirements of the at least four sensors and a lifespan of the power source. In addition, processor 40 may receive sensor data from the sensor elements and communicate vital sign status of the pet animal to a remote location. The processor 40 may reach overall conclusions as to whether the pet has a particular medical condition by accessing databases and utilizing software containing diagnostic algorithms.

Particular features described in the context of one embodiment may be able to be incorporated into other embodiments for which that feature was not specifically mentioned.

The following are non-limiting examples of vital sign and/or other physiological data for dogs acquired from sensor elements 30. In general, dog sounds recorded by a microphone may be combined with information from other sensor elements 30 regarding dog postures and dog movements and this may be further combined with information from other sensor elements 30 such as temperature, respiration rate and pulse and other available data such as the time of day, the ambient temperature, the pet's normal behavior, the context etc. The processor 40 may reach conclusions about the presence of a high probability of medical conditions suffered by dogs or cats or other pet animals, such as hypothermia, hyperthermia, slow heart rate, normal or abnormal sinus arrhythmia, ear infections, torn ligaments, gastric dilatation, dyspnea, gastritis, pruritus and osteoarthritis. For example, hypothermia occurs when heat loss/output exceeds heat production. It can happen in cold weather, especially to small or sick animals, or under sedation or anesthesia. If low body temperature is recorded by the sensor elements 30 at a time when the ambient temperature is very cold, an alert may be sent. In another case, if a slower than normal heart rate is detected by sensor elements 30 in a pet animal the movements of the pet animal may be checked to determine if an alert needs to be sent. In general, the pulse rate may be compared to the respiration rate over time to see if the heart rate increases when the animal takes a breath. Regarding ear infections in a dog, if the sensor 30 input indicates movements consistent with an ear infections and the microphone sensor indicates sounds of pain when the ears are touched, an alert may be sent. Inflammation of the bones and joints is a common disease of older dogs. If the sensor input indicates decreased or change in activity relative to the time of day and sounds of pain, an alert may be transmitted.

Applicant has conducted experiments in which particular configurations of the acoustic concentrators and particular configurations of the acoustic concentrators were tested. Both the size and the configuration of the base ends were varied. Surprisingly, Applicant found that having the base end of the acoustic concentrators and balancers shaped in the form of crossing lines, for example perpendicular diameters at the base end of a hollow acoustic concentrator/balancer, with a circular perimeter, as shown in FIG. 4B, may reduce unwanted oscillations while still minimizing other parasitic decay effects (such as "shelf") and may yield a stable signal.

Applicant's experiments of various configurations and combinations of configurations between the bumps on the working surface (acoustic concentrators) and the bumps on the rear surface (acoustic balancers 24 yielded some unexpected conclusions. For example, the X-shaped base end form may be the best choice for the working surface of the elastomer, in certain preferred embodiments. The height of the X-shape acoustic concentrator or balancer may not produce a significant impact on the quality of the signal, but there may be a slight advantage for greater height of the bump (on either the working surface or on the rear surface). Typically, the range of heights tested varied from 5 millimeters to 7 millimeters. In addition, the configuration of the bumps on the rear surface (acoustic balancers) may have a strong impact on the quality of the signal produced. Solid non-spherical shaped referred to as "bulky forms", as illustrated in FIGS. 8A-8B, may have some positive effect of signal attenuation so as to reduce or eliminate or minimize parasitic oscillations. On the other hand, as the back side bump is heavier (less hollow) the pulses were found to be shorter, which may be a disadvantage since it makes processing of the signal more complicated. Preferably, there should be a good balance between the mass of the bump on both working and rear surfaces and the bump form in order to achieve an optimal signal.

Reference to a semi-cylindrical acoustic concentrator 22 or balancer 24, as used herein, means that the bump comprising the concentrator 22 or balancer 24 has a shape like a half-cylinder that comes into being when a cylinder has been cut in two along its length (longitudinally). The bisecting plane may be used as the plane at the concentrator base end 23 of the acoustic concentrator 22 or at the balancer base end 27 of the acoustic balancer 24. The term "about" means plus or minus 5%.

This patent application hereby incorporates by reference in its entirety the Applicant's previously filed U.S. Patent Application having Publication No. 20130014706 published Jan. 17, 2013 having the Title "Pet Animal Collar for Health and Vital Signs Monitoring, Alert & Diagnosis" and having a filing date of Feb. 21, 2012.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. An acoustically enhanced collar for non-invasively monitoring vital signs of a pet animal, wherein the pet animal is a dog or cat, the collar comprising:

a band of elastic material having a first surface configured to wrap around a portion of the pet animal and a second surface facing in an opposite direction to the first surface;

sensor elements situated at one or more regions along a circumference of the band, the sensor elements including:

(A) at least one acoustic sensor configured to measure at least one of heart rate and respiration rate and configured to output at least one signal representing vital sign data for the at least one of heart rate and respiration, the at least one acoustic sensor including at least one piezoelectric element embedded in the band, at least one acoustic concentrator integrally formed with the band and projecting, toward a body portion of the pet animal from the first surface at the one or more regions along the circumference, the at least one acoustic concentrator conveying an acoustic signal to the band containing the at least one piezoelectric element;

at least one acoustic balancer integrally formed with the band and projecting from the second surface at the one or more regions along the circumference, the at least one acoustic balancer situated at the region along the circumference at least partly behind the at least one acoustic concentrator, the at least one acoustic balancer configured to balance the acoustic signal conveyed by the at least one acoustic concentrator against noise and thereby increase a readability of an acoustic signal provided to the at least one acoustic sensor, each of the at least one acoustic concentrator tapered inwardly from a concentrator base end to a concentrator top end, the concentrator top end distal from the band, and each of the at least one acoustic balancer tapered inwardly from a balancer base end to a balancer top end, the balancer top end distal from the band, each of the at least one acoustic concentrator configured in shape to penetrate a fur of the pet animal at an area of an artery of the pet animal and conduct the at least one signal from a neck portion of the pet animal to the at least one acoustic sensor; and (B) one or both of:

(i) one or more temperature sensors to measure temperature and (ii) at least one of an accelerometer, a gyroscope and a magnetometer sensor to measure at least one of movement and posture.

2. The collar of claim 1, wherein a region of the one or more regions along the circumference where the at least one acoustic concentrator is located overlaps with a region of the one or more regions along the circumference where the at least one acoustic balancer is located.

3. The collar of claim 1, wherein the at least one acoustic concentrator and the at least one acoustic balancer are made of a same material as the band.

4. The collar of claim 1, wherein the at least one acoustic concentrator and the at least one acoustic balancer are circular in at least one dimension.

5. The collar of claim 1, wherein the at least one acoustic concentrator and the at least one acoustic balancer are configured such that a signal-to-noise ratio of the at least one signal is from 20 decibels to 40 decibels.

6. The collar of claim 1, wherein the at least one acoustic concentrator and the at least one acoustic balancer are configured such that a signal-to-noise ratio of the at least one signal is at least 20 decibels.

7. The collar of claim 1, wherein at least one of the following is true: (i) each of the at least one acoustic concentrator is longest in a dimension perpendicular to the piezoelectric element, (ii) each of the at least one acoustic balancer is longest in a direction perpendicular to the piezoelectric element.

8. The collar of claim 1, wherein the sensor elements are configured to measure both posture and movement.

9. The collar of claim 1, wherein the at least one acoustic concentrator comprises at least three acoustic concentrators.

10. The collar of claim 1, wherein the at least one piezoelectric element comprises two physically separated piezoelectric elements connected electrically, each of the two physically separated piezoelectric elements is positioned on opposite sides of the neck portion of the animal.

11. The collar of claim 1, wherein the one or more temperature sensors includes a body temperature sensor and an ambient temperature sensor.

12. The collar of claim 1, wherein the sensor elements are configured to measure at least the following bioparameters: temperature, heart rate, movement and posture.

13. The collar of claim 1, wherein the sensor elements are configured to measure temperature, heart rate, respiration rate, posture and movement.

14. The collar of claim 1, wherein a processor executes algorithms to interpret an interdependence of the vital sign data to arrive at a tentative diagnosis.

15. The collar of claim 1, wherein the at least one of an accelerometer, a gyroscope and a magnetometer comprises an accelerometer for sensing posture and movement of the pet animal and outputting at least one signal representing vital sign data for the posture and movement of the pet animal.

16. The collar of claim 1, wherein each of the at least one acoustic concentrator is tapered inwardly along at least half a distance from the concentrator base end to the concentrator top end and each of the at least one acoustic balancer is tapered inwardly along at least half a distance from the balancer base end to the balancer top end.

17. A system comprising:
I. an acoustically enhanced collar for non-invasively monitoring vital signs of a pet animal, wherein the pet animal is a dog or cat, the collar comprising:
a band of elastic material having a first surface configured to wrap around a portion of the pet animal and a second surface facing in an opposite direction to the first surface;
sensor elements situated at one or more regions along a circumference of the band, the sensor elements including:
(A) at least one acoustic sensor configured to measure at least one of heart rate and respiration rate and configured to output at least one signal representing vital sign data for the at least one of heart rate and respiration, the at least one acoustic sensor including at least one piezoelectric element embedded in the band,
at least one acoustic concentrator integrally formed with the band and projecting, toward a body portion of the pet animal from the first surface at the one or more regions along the circumference, the at least one acoustic concentrator conveying an acoustic signal to the band containing the at least one piezoelectric element;
at least one acoustic balancer integrally formed with the band and projecting from the second surface at the one or more regions along the circumference, the at least one acoustic balancer situated at the region along the circumference at least partly behind the at least one acoustic concentrator, the at least one acoustic balancer configured to balance the acoustic signal conveyed by the at least one acoustic concentrator against noise and thereby increase a readability of an acoustic signal provided to the at least one acoustic sensor,
each of the at least one acoustic concentrator tapered inwardly from a concentrator base end to a concentrator top end, the concentrator top end distal from the band, and each of the at least one acoustic balancer tapered inwardly from a balancer base end to a balancer top end, the balancer top end distal from the band,
each of the at least one acoustic concentrator configured in shape to penetrate a fur of the pet animal at an area of an artery of the pet animal and conduct the at least one signal from a neck portion of the pet animal to the at least one acoustic sensor; and
(B) one or both of:
(i) one or more temperature sensors to measure temperature and
(ii) at least one of an accelerometer, a gyroscope and a magnetometer sensor to measure at least one of movement and posture; and
II. a processor configured by software to execute algorithms to interpret an interdependence of the vital sign bioparameter data to arrive at a tentative diagnosis of the pet animal and wherein the vital sign bioparameter data includes at least two of (i) at least one of heart rate and respiration rate, (ii) temperature and (iii) at least one of movement and posture.

18. The system of claim 17, wherein each of the at least one acoustic concentrator is tapered inwardly along at least half a distance from the concentrator base end to the concentrator top end and each of the at least one acoustic balancer is tapered inwardly along at least half a distance from the balancer base end to the balancer top end.

19. A system comprising:
I. an acoustically enhanced collar for non-invasively monitoring vital signs of a pet animal, wherein the pet animal is a dog or cat, the collar comprising:
a band of elastic material having a working surface configured to wrap around a portion of the pet animal and a rear surface facing in an opposite direction to the working surface;
sensor elements situated at one or more regions along a circumference of the band, the sensor elements including:
(A) at least one acoustic sensor configured to measure at least one of heart rate and respiration rate and configured to output at least one signal representing vital sign data for the at least one of heart rate and respiration, the at least one acoustic sensor including at least one piezoelectric element embedded in the band,
at least one acoustic concentrator integrally formed with the band and projecting, toward a body portion of the pet animal from the working surface at the one or more regions along the circumference, the at least one acoustic concentrator conveying an acoustic signal to the band containing the at least one piezoelectric element;

at least one acoustic balancer integrally formed with the band and projecting from the rear surface at the one or more regions along the circumference, the at least one acoustic balancer situated at the region along the circumference at least partly behind the at least one acoustic concentrator, the at least one acoustic balancer configured to balance the acoustic signal conveyed by the at least one acoustic concentrator against noise and thereby increase a readability of an acoustic signal provided to the at least one acoustic sensor, each of the at least one acoustic concentrator tapered inwardly from a concentrator base end to a concentrator top end, the concentrator top end distal from the band, and each of the at least one acoustic balancer tapered inwardly from a balancer base end to a balancer top end, the balancer top end distal from the band each of the at least one acoustic concentrator configured in shape to penetrate a fur of the pet animal at an area of an artery of the pet and conduct the at least one signal from a neck portion of the pet to the at least one acoustic sensor; and (B) one or both of:
  (i) one or more temperature sensors to measure temperature and
  (ii) at least one of an accelerometer, a gyroscope and a magnetometer sensor to measure at least one of movement and posture; and II. one or more processors, wherein the sensor elements and the one or more processors are configured to detect at least three of the following: an indication of the dog lying down laterally, an indication of the dog lying down sternally (head up/down), an indication of the dog sitting, an indication of the dog standing on four legs and an indication of the dog exhibiting a posture associated with eating or drinking.

20. The system of claim 19, wherein each of the at least one acoustic concentrator is tapered inwardly along at least half a distance from the concentrator base end to the concentrator top end and each of the at least one acoustic balancer is tapered inwardly along at least half a distance from the balancer base end to the balancer top end.

* * * * *